United States Patent [19]

Lipatova et al.

[11] 4,057,535

[45] Nov. 8, 1977

[54] ADHESIVE FOR GLUING TOGETHER SOFT BODY TISSUES

[76] Inventors: Tatyana Esperovna Lipatova, ulitsa Vladimirskaya, 51/53, kv. 22; Roman Alexandrovich Veselovsky, Kharkovskoe shosse, 21/3, kv. 179; Georgy Alexandrovich Pkhakadze, ulitsa Nikolskobotanicheskaya, 3, kv. 8, all of Kiev, U.S.S.R.

[21] Appl. No.: 676,989

[22] Filed: Apr. 14, 1976

[51] Int. Cl.$^2$ .................. C08G 18/32; A61K 31/74; A61L 17/00; C08G 18/18
[52] U.S. Cl. .................. 260/77.5 AC; 128/335.5; 260/2.5 AD; 260/75 NC; 260/75 NT; 260/75 AT; 260/77.5 SS; 260/77.5 MA; 424/78
[58] Field of Search .................. 260/75 NC, 77.5 NC, 260/77.5 SS, 77.5 AC, 77.5 MA, 77.5 HQ, 75 NT, 77.5 AT

[56] References Cited

U.S. PATENT DOCUMENTS

| 3,202,728 | 8/1965 | Kohn | 260/858 |
| 3,222,303 | 12/1965 | Hampson | 260/75 NC |
| 3,580,868 | 5/1971 | Diehr et al. | 260/77.5 NC |
| 3,763,274 | 10/1973 | Wang et al. | 260/858 |
| 3,860,673 | 1/1975 | Lawrence | 260/77.5 NC |

*Primary Examiner*—H.S. Cockeram
*Attorney, Agent, or Firm*—Steinberg & Blake

[57] ABSTRACT

An adhesive for gluing together soft body tissues, which has the following composition, wt.%:

aromatic diisocyanate, from 1 to 50
macrodiisocyanate of the general formula

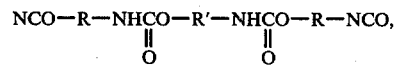

where
R is an aromatic diisocyanate radical;
R' is a polyether or polyester radical, from 98.9 to 30;
2,4,6-tris(dimethylaminomethyl)phenol, from 0.1 to 20.

The proposed adhesive is effective for gluing together soft body tissues in a tissue fluid medium; it is highly elastic; it is rapidly intergrown with live tissues and eliminated from the body; and it has a controlled setting time.

6 Claims, No Drawings

ADHESIVE FOR GLUING TOGETHER SOFT BODY TISSUES

The present invention relates to medical adhesives and, more particularly, to an adhesive for gluing together soft body tissues.

The proposed adhesive may find application in surgery for gluing together soft tissues rather than joining them by suturing.

There exists a range of adhesives currently in wide use for gluing together soft body tissues, which are based on cyanoacrylic esters such as methyl-, ethyl-, butyl-, isobutyl- or hexyl-2-cyanoacrylates. These known adhesives are convenient in handling and polymerize quickly; however, a number of inherent disadvantages prevent their wide use in medical practice. The chief of these disadvantages are as follows: reduced adhesiveness in the presence of excess moisture; inadequate elasticity and rigidity of the adhesive film; and local histotoxic effect (particularly marked in the case of adhesives on the basis of methyl- and ethylcyanoacrylates).

It is an object of the present invention to provide an adhesive for gluing together soft body tissues which is effective in a medium of tissue fluids.

It is another object of the present invention to provide an adhesive distinguished by virtue of high elasticity and controlled setting time.

It is a further object of the present invention to provide an adhesive which is quickly intergrown with live tissues and eliminated from the body.

These and other object are attained by the provision of an adhesive for gluing together soft body tissues which, in accordance with the invention, has the following composition wt.%:

aromatic diisocyanate, from 1 to 50
macrodiisocyanate of the general formula

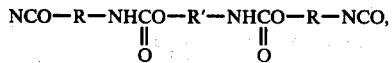

where
R is an aromatic diisocyanate radical
R' is a polyether or polyester radical, from 98.9 to 30
2,4,6-tris(dimethylaminomethyl)phenol, from 0.1 to 20.

The isocyanate compounds cause the proposed adhesive to set under the effect of moisture invariably present on the surfaces being glued together.

By varying the proportion of the 2,4,6-tris(dimethylaminomethyl)phenol component of the proposed adhesive, the setting time thereof can be controlled.

Since the isocyanate groups react with the 2,4,6-tris(dimethylaminomethyl)phenol, the set adhesive contains no low-molecular compounds capable of diffusing out and exerting a toxic effect on the tissues being glued together. Besides, the products produced by reaction of the 2,4,6-tris(dimethylaminomethyl)phenol with the aromatic diisocyanate or the macrodiisocyanate exhibit marked diphilic properties, i.e. they are surface-active agents promoting the adhesion and gluing together of tissues in a medium of tissue fluids.

While setting, the adhesive liberates carbon dioxide which forms minute pores in the adhesive body wherethrough burgeoning live tissues can advance.

As the ester or ether and urethane groups of the adhesive show poor hydrolytic stability, the adhesive readily breaks down to be eliminated from the body.

Such adhesive properties as strength, elasticity, hydrophily, porosity and resorption rate are controlled by the choice of aromatic diisocyanate, the composition of the macrodiisocyanate component as well as by the ratio of the aromatic diisocyanate to the macrodiisocyanate.

4,4¹-diphenylmethanediisocyanate or napthylenediisocyanate used as the aromatic diisocyanate imparts improved strength to the adhesive, whereas toluylenediisocyanate imparts added elasticity thereto.

In order to boost the rate of adhesive resorption in the body, it is recommended to make use of a macrodiisocyanate of the general formula presented above, containing a radical of toluylenediisocyanate, 4,4¹-diphenylmethanediisocyanate or napthylenediisocyanate and a polyester group such as polydiethyleneglycoladipate, polyethyleneglycoladipate or polydiethyleneglycolsebacate.

In order to improve the hydrophilic nature of the adhesive, the macrodiisocyanate component should preferably contain radicals of said aromatic diisocyanates and a polyether group such as polyhydroxyethyleneglycol or the copolymer of propyleneglycol with ethyleneglycol. If the macrodiisocyanate contains a polytetramethyleneglycol radical or a radical of the copolymer of propyleneglycol with tetramethyleneglycol, the adhesive acquires improved rigidity, whereas a polyhydroxypropyleneglycol radical adds to the elasticity of the adhesive suture.

For sealing intestinal and bronchial fistulas, gluing together muscles, renal and lupatic parenchyma and intestines, as well as for pasting skin and reinforcing sutures, the following compositions of the adhesive are recommended, wt.%:

(a)
toluylenediisocyanate, 10
macrodiisocyanate of the formula, 70

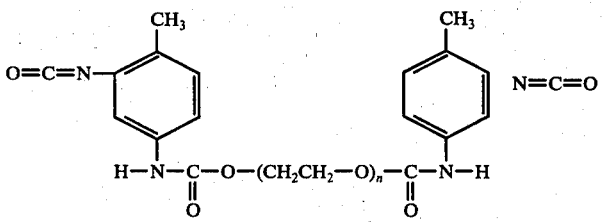

2,4,6-tris(dimethylaminomethyl)phenol, 20;

(b)
toluylenediisocyanate, 10
macrodiisocyanate of the formula

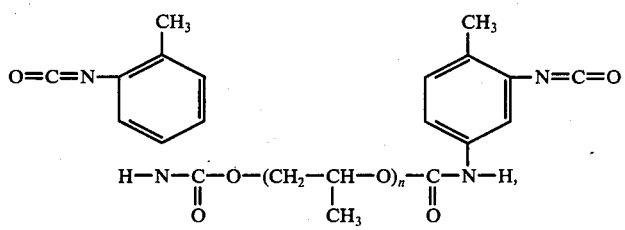

2,4,6-tris(dimethylaminomethyl)phenol, 10.

The proposed adhesive was tested for its effectiveness as a means of gluing together animal tissues in plastic repair of aponeurosis of the anterior abdominal wall according to Sapezhko, as well as for closing colonic fistulas.

The technique of plastic repair of aponeurosis was as follows: under local anaesthesia with a 0.25-percent aqueous solution of Novocaine, the rabbit's skin and the muscular-aponeurotic layer of the anterior abdominal wall were incised over a length of 5 to 6 cm, the peritoneum was separated by blunt dissection from the intimately adjacent muscles by a distance of 1.5 to 2 cm, after which the muscles were joined according to Sapezhko (lap-joined) previously applying to the surface of one of the muscles adhesive of the following composition, wt.%:

toluylenediisocyanate, 10
macrodiisocyanate containing toluylenediisocyanate and polyhydroxypropyleneglycol groups, 80
2,4,6-tris(dimethylaminomethyl)phenol, 10.

No thorough drying of the surfaces being glued together was needed.

All in all, 79 operations on the anterior abdominal wall were performed, using various methods of joining the tissues.

In all cases where the tissues were joined by suturing and suturing-cum-gluing, the joined tissues stuck together. In all rabbits sacrificed postoperatively within the terms indicated in the table that follows, the adhesive sutures proved reliable.

In 1 animal of the 19 subjected to plastic surgery with the aid of the proposed adhesive of the above-mentioned composition, the joined tissues got detached on the second day after the operation. At autopsy no suppuration of the wound or pronounced inflammation was revealed; the polymerized adhesive film was concentrated primarily on the lower tissue sheath.

Of the 18 rabbits subjected to surgery by use of the ethyl-2-cyanoacrylate adhesive, the adhesive suture proved incompetent on the 4th day postoperatively in 1 animal. At autopsy, suppuration of the wound was observed.

The rest of the animals in which the anterior abdominal wall tissues were glued together, successfully endured the operation and showed no complications in the postoperative period. The animals were sacrificed within the terms indicated in the table; the sutures were found to be reliable.

The strength of the sutures was checked immediately upon application of the adhesive, in 2 hours' time, on the 3rd and 7th days and after a month postoperatively. During each check, 4 to 6 tests were run using both the proposed adhesive and the ethyl-2-cyanoacrylate glue. The test data are given in the following table.

| Technique of suturing | Testing time | | | | |
|---|---|---|---|---|---|
| | immediately | in 2 hr | in 3 days | in 7 days | in 30 days |
| Proposed adhesive | 4 | 6 | 7 | 7 | 5 |
| Ethyl-2-cyanoacrylate adhesive | 4 | 6 | 7 | 6 | 5 |
| Silk | — | — | 3 | — | 5 |
| Silk-cum-proposed adhesive | — | — | 2 | — | 5 |
| Silk-cum-ethyl-2-cyanoacrylate adhesive | — | — | 2 | — | 5 |

No strength tests were carried out in the late follow-up period, for after 30 days the tissues must be held together not only by the adhesive but also due to the burgeoning of tissue elements into the adhesive film.

Use was made of a widely applied technique of determining the ultimate strength of adhesive compositions, viz. shear strength testing. To determine the shear strength of the adhesive suture, the glued-together tissues were subjected to tensile tests on an automatic tensile tester.

Both types of adhesive were found to provide a fairly similar level of shear strength, in spite of the fact that the ethyl-2-cyanoacrylate adhesive was used to join thoroughly dried tissues, whereas the adhesive of the present invention was employed in a medium of tissue fluids. For the ethyl-2-cyanoacrylate adhesive, the shear strength was 882 g/sq.cm.; for the adhesive of this invention, 796 g/sq.cm. Some tissue specimens joined with the proposed adhesive withstood loads of up to 3,220 g.

Microscopic studies revealed differences between the tissues glued together with the proposed adhesive and the ethyl-2-cyanoacrylate one as far as the course of regeneration is concerned.

On the third postoperative day, traces of both adhesives were clearly discernible with the naked eye. The tissues joined with the adhesive of this invention were practically normal in colour, whereas those glued together with the ethyl-2-cyanocrylate adhesive had a grayish-cyanotic tint. The latter tissues were also found to be inferior in elasticity to the tissues joined with the proposed adhesive.

Colonic fistulas were simulated in the following manner. Under local anaesthesia, rabbits were subjected to median laparotomy. A perforation was drilled in the loop of the large intestine. A PVC tube was inserted into the intestinal lumen, attached by suturing to the wall of the colon and led through a counter-opening to the external surface of the anterior abdominal wall. In 2 weeks' time, after a connective-tissue frame defining a fistular channel had been formed around the PVC tube, the latter was withdrawn. The fistula was closed by introducing adhesive of the above composition into the fistular channel via a probe, the adhesive polymerizing in the fistular channel. This technique of medicamental treatment of colonic fistulas proved highly effective, for in this case the adhesive doubled as a sealing compound. Of the 58 rabbits subjected to tests of the latter type, only one registered a relapse. Closure reliability testing by pneumopressure initiated on the 3rd postoperative day indicated that the glued-together section was stronger than the normal sections of the intestine.

The proposed adhesive was tested for local histotoxic effect by applying the same to the surface of organs.

The experiments used chinchilla rabbits and albino rats weighing 2 to 2.5 kg and 100 to 150 g, respectively. Under ether anaesthesia, the animals were subjected to laparotomy under sterile conditions, and the proposed adhesive was applied to the surfaces of the liver, kidney, large and small intestine at the rate of 40 to 60 mg per 30 sq.mm. of tissue area. The adhesive was likewise applied to the surface of the gluteal muscle (after dissecting the fascia). The muscles and the skin were sutured in layers with silk. The animals were sacrificed postoperatively in 1 and 6 hours, 1, 4, 7, 14, 30 and 60 days and 6 months. The experimental group consisted of 54 rabbits and 28 rats, animals subjected to laparotomy under ether anaesthesia without adhesive application serving as controls.

The tissue segments treated with the adhesive and the remnants of the adhesive film were studied histologically and histochemically. The sections were stained with hematoxylineosin, according to van-Giseon, according to Brachet (RNA determination under ribonuclease control), according to Feulgen (DNA determination), according to Heidenheine, with Sudan dyes III and IV and Black B.

The results indicated that in all the organs studied, 6 hours after the operation single eosinophilic polymorphonuclear leukocytes emerged directly under the adhesive film. 24 hours after the operation, their number grew somewhat, particularly in the muscle as well as in the large and small intestines. On the 4th postoperative day, under the yellow adhesive film rich in pores filled with plasma and fibrinous material there was formed an infiltrate composed of lymphocytes, eosinophils, macrophages, plasmacytes and young fibroblasts as well as occasional giant cells of foreign bodies in the formative phase. Already at that time the cellular infiltrate was more pronounced on the muscle and the bowels and contained a higher count of eosinophilic leukocytes than that on the kidney and the liver. The cytoplasm of the young fibroblasts was pyroninophilic, the infiltrate cell nuclei were rich in DNA. On the 7th day, maturing fibroblasts oriented along the polymeric film were observed under the film about the periphery of the cellular infiltrate. Delicately fuchsinstained collagen fibrils, as yet non-oriented, emerged between said fibroblasts. In the area adjacent to the polymer the cellular infiltration persisted, though the leukocyte count dropped somewhat on the liver and the kidney. The young fibroblasts in this zone were arranged normally to the polymeric film, their processes sort of being embedded in the film pores. The cellular elements of this zone were characterized by highly pyroninophilic cytoplasm with occasional giant cells of foreign bodies.

From the 14th day onwards, two zones emerged around the polymer: the 1st zone immediately adjacent the polymer was composed of yound granulation tissue containing young fibroblasts, macrophages and lymphocytes. On the liver and the kidney, the eosinophilic leukocytes almost totally disappeared from this zone, though remaining present in an appreciable number on the intestines and the muscle. The giant cells of foreign bodies whose number grew as against the 7th day were disposed immediately adjacent the adhesive fragments. It should be further noted that the yound granulation tissue grew into the polymer pores. Zone II was a capsule formed by mature connective tissue. The fibroblasts here were oriented in parallelism with the polymeric film; their cytoplasm was less pyroninophilic; bunches of brightly fuchsinophilic collagen fibres were disposed between the fibroblasts. The connective tissue was shot through with a network of regenerative blood vessels.

In the period from the 2nd to the 6th month after the operation, the polymer underwent further fragmentation and more tissue grew thereinto. The cellular composition of the granulation tissue changed somewhat: the eosinophilic leukocytes disappeared altogether; the lymphocyte count dropped; the giant cells of foreign bodies grouped around the residual adhesive fragments, mostly large fragments interspersed with a certain number of small ones clearly discernible if stained with Sudan III-IV.

Alongside the emergence and subsequent transformation of granulation tissue, the parenchyma and stroma of the organs studied likewise underwent alterations under the adhesive film. Thus, in the liver tissue observed from the 6th hour to the 7th day postoperatively, the hepatocytes in the vicinity of the polymeric film showed dystrophic changes, primarily of the granular dystrophy type. In the remote sections of the liver, changes of this sort were observed but in single cells. The central veins and capillaries were distended and filled with blood. By the 14th day, the state of the hepatic cells was back to normal; and by the 1st or 2nd month postoperatively, the liver parenchyma of the experimental animals was indistinguishable from that of the controls.

Histologically, the kidney was characterized in the early postoperative period by the filling with blood of the renal glomerula and the dystrophic alterations of the epithelium of the cortical tubules. In the late follow-up period, by the 1st to 2nd month, the renal structure normalized.

In the large and small intestines, the intestinal stroma underwent no substantial changes in the early follow-up period. By the 7th day, the polymorphocellular infiltrate penetrated the muscle layers in but a few isolated cases. The epithelium of the villi exhibited in places manifestations of granular dystrophy. By the end of the 1st or 2nd month, the epithelium was back to normal; fibrous tissue emerged over the cellular infiltration areas.

The muscular tissue showed alterations only within the first 4 days postoperatively, and even these were hardly noticeable: emergence of granular dystrophy areas and partial disappearance of lateral striation. Subsequently, these alterations were not observed.

As follows from literary data, upon implantation of porous material granulation tissue grows into the implant pores. Solid impants are covered with connective tissue only about the periphery thereof.

The adhesive film utilized in the research being reported may be viewed as a porous implant. The marked cellular reaction and the high levels of RNA and DNA in the infiltrate cells testify to the unimpaired synthesizing ability of the cellular elements disposed in the vicinity of the polymer which, judging by the cellular reaction, exhibits very little, if any, toxicity.

The dynamics of excretion of the material produced in the biodestruction of the proposed adhesive was studied by use of a radioisotopic tracer ($^{14}C$).

The experimental animals were albino rats weighing 100 to 120 g. Under ether anaesthesia, the gluteal muscle was incised under sterile conditions and $^{14}C$-labelled adhesive was pipetted into the cut at the rate of 0.06 micrograms per 1 kg of body weight, after which the wound was sutured. The animals were sacrificed by decapitation within 3 hours, 1, 5, 10 and 15 days, 1, 2, 3, 4 and 6 months. Studies were performed on the brain, heart, liver, kidneys, spleen, lungs, skeletal muscle, blood serum, urine (from the bladder) and faeces (from the rectum) of the sacrificed animals. The blood serum and the urine were applied in respective amounts of 0.3 and 0.1 ml to standard targets. The other tissues were minced with scissors, dried in a desiccator at a temperature of 105° C. to a constant weight, pulverized to a fine powder in porcelain mortars, and applied in 15-mg aliquots to the targets.

The radioactivity was determined with the aid of an end-window counter. In each series of experiments, 5 to 8 animals were used.

As shown in these studies, already in the early follow-up period (3 hours, 1 day), the blood serum registered considerable radioactivity, testifying to the presence of adhesive biodestruction material in the animals' body. 1 to 5 days later, radioactive products were fairly intensively excreted with urine and faeces. A radioactive background was found in the tissues under study, its level being slightly higher in the organs that can take a direct part in the elimination of adhesive particles from the body, namely the kidneys and the lungs.

10 to 15 days later, the process of adhesive elimination, and hence adhesive suture resorption, ground almost to a halt. Yet, the tissues and excretions showed some, though insignificant, radioactivity for 45 days after labelled adhesive had been administered to the animals.

2 months after the experiment, several organs showed a trend towards a higher radioactive background; at about the same time the adhesive diminshed in particle size.

In 3 months' time, no adhesive could be detected at the application site. The radioactivity of the excretions as well as of all the organs and tissues studies, except for the skeletal muscles at the adhesive application site, was either nil or insignificant. By the 4th and 6th months postoperatively, all objects studied were found to be non-radioactive.

On the basis of our data, the process of resorption of the proposed adhesive may be broken down into 3 stages. At the first stage which roughly lasts 1 week after the operation, the adhesive undergoes relatively fast hydrolysis to be eliminated from the body, the process being obviously promoted by the extensive contact of the adhesive material with the wound surface. In the subsequent period — reparative-regenerative process of the wound and partial encapsulation of the adhesive particles — the resorption and elimination of the adhesive biodestruction products slows down. In all probability, the duration of the latter stage is subject to considerable variation depending on the quantity and site of application of the adhesive. In experiments on rabbits, the process of adhesive resorption was histologically observed to last 10 to 12 months.

The third stage characterized by a somewhat stepped-up process of adhesive elimination, again depending on the quantity of adhesive administered to the animal, its particle size and degree of encapsulation, may taken place within various times postoperatively. In the experiments of the mentioned series it was observed between the 2nd and 3rd months postoperatively.

The products of adhesive biodestruction were not found to accumulate either in the organs or tissues.

Biochemical investigation of the muscular tissue (selected as an object of detailed study for reasons of being a predominant element in the body most likely to sustain accidental or surgical trauma) aimed at revealing the ways of adenosine triphosphoric acid resynthesis, indicated that, when the skeletal muscles were joined with the adhesive of this invention, the reparative-regenerative process obeyed the general laws. The following characteristics were determined in the 189 experiments of the latter series: (a) level and specific radioactivity of adenosine triphosphoric acid, adenosine diphosphoric acid and creatine phosphate; (b) concentration of lactic acid and glycogen; (c) activity of creatine kinase; (d) oxygen uptake; and (e) intensity of regeneration of various muscle protein fractions.

Immunological investigations (double diffusion in agar gel; anaphylactic reaction with desensitization on guinea pigs) indicated that the antigenic composition of the skeletal muscles joined with the adhesive of this invention was indistinguishable from that of the muscles joined with silk. Thus, destruction of the polymeric adhesive film did not trigger haptogenic immune reactions.

Clinical trials were run using the adhesive of the invention of the following composition, wt.%:

toluylenediisocyanate, 10
macrodiisocyanate containing toluylenediisocyanate and polyhydroxypropyleneglycol radicals, 80
2,4,6-tris(dimethylaminomethyl)phenol, 10.

The adhesive of the foregoing composition was applied in 19 cases for medicamental treatment of intestinal fistulas. To this end, having carried out the toilet of the fistular channel, adhesive was introduced with a syringe into the fistular channel via a probe.

The adhesive polymerized in the fistular channel and expanded somewhat, filling up the fistular channel and sealing same. In 16 cases the fistula was securely closed by this method. In 3 cases relapses occured, though in 2 of them the fistulas were closed by repeated administration of adhesive. During the clinical follow-up period which lasted for 6 to 24 months, the patients had no complaints.

The proposed adhesive of the foregoing composition was employed for reinforcing cerebral aneurysm with a broad neck and, hence, incapable of being radically removed. After exposing the vessel, adhesive was applied to the aneurysmal dilatation zone with a swab. Within 5 to 7 minutes, a highly elastic porous polymeric film was formed on the vessel surface, defining a sort or polymeric framework around the affected vessel which maintained the normal lumen of the vessel. 5 operations of this kind were performed. During the follow-up period which lasted for 3 to 6 months, the general status of the patients was satisfactory.

The proposed adhesive was also subjected to clinical trials for extrathoracic closure of bronchial fistulas, adhesive being delivered to the fistulated bronchial stump through a probe via a bronchoscope.

With the aid of a syringe attached to the probe adhesive was supplied into the bronchus, wherein the adhesive polymerized to assume the bronchus shape and thereby to securely close the tissue defect. This method permitted avoiding major surgery, viz. thoracotomy. All in all, 22 operations of the latter kind were performed, with total success achieved in 19 cases.

The proposed adhesive is prepared in the following way.

The adhesive is prepared by mixing the following components in the following amounts, wt.%:

aromatic diisocyanate, from 1 to 50
macrodiisocyanate of the general formula given hereabove, from 98.9 to 30
2,4,6-tris(dimethylaminomethyl)phenol, from 0.1 to 20.

The proportion of the aromatic diisocyanate should be within 1 to 50 percent by weight. A level of the aromatic diisocyanate below 1 percent by weight impairs the setting ability of the adhesive and detracts from its porosity and strength, a quantity of the aromatic diisocyanate above 50 percent by weight reduces the elasticity of the adhesive and brings about intensive liberation of gas upon setting.

The macrodiisocyanate component should account for from 30 to 98.9 percent by weight. Below this range, the adhesive loses some of its strength and elasticity; whereas more than 98.9 percent by weight of the macrodiisocyanate prolongs the setting time and causes incomplete setting.

Reduction of the level of 2,4,6-tris(dimethylaminomethyl) phenol below 0.1 percent by weight prolongs the setting time of the adhesive; whereas more than 20 percent by weight of this component detracts from the strength of the adhesive.

The macrodiisocyanate of the general formula given hereabove is obtained by admixing a polyether or a polyester with an aromatic diisocyanate, said components being taken in amounts such that the ratio of the —OH and —NCO groups is equal to 1:2.

The polyether may be polyhydroxypropyleneglycol, polyhydroxyethyleneglycol, polytetramethyleneglycol, polypentamethyl eneglycol, polyhexamethyleneglycol, the copolymer of ethyleneglycol with propyleneglycol, the copolymer of propyleneglycol with tetramethyleneglycol, or the copolymer of ethyleneglycol with tetramethyleneglycol.

The polyester may be e.g. polydiethyleneglycoladipinate, polyethyleneglycoladipinate, polydiethyleneglycolsebacate, polypropyleneglycoladipinate, or polyethyleneglycoladipinatephthalate.

The aromatic diisocyanate may be constituted by toluylenediisocyanate, 4,4'-diphenylmethanediisocyanate, naphthylenediisocyanate, 1,5-napthylenediisocyanate, 3,3'-dimethoxy-4,4'-biphenylenediisocyanate, 3,3'-dimethyl-4,4'-biphenylenediisocyanate, phenylenediisocyanate, or 4,4'-biphenylenediisocyanate.

The macrodiisocyanate production is monitored by the concentration of the isocyanate groups in the mixture. The macrodiisocyanate synthesis temperature should not exceed 80° C.

The macrodiisocyanate thus obtained is admixed with an aromatic diisocyanate, e.g. the foregoing diisocyanate. If the aromatic diisocyanate is the same as is employed in the synthesis of the macrodiisocyanate, then a required excessive quantity of said diisocyanate can be introduced in advance in the course of macrodiisocyanate synthesis.

The 2,4,6-tris(dimethylaminomethyl)phenol is added to the composition immediately prior to adhesive application to the tissues to be glued together.

In an unset state, the proposed adhesive is a glycerol-like clear liquid which sets when applied to moist animal tissues. The set adhesive is a white elastic foamed material. As the adhesive sets, cells 0.1 to 0.5 mm in diameter are formed therein, promoting tissue burgeoning through the adhesive and adhesive resorption.

The set adhesive has a tensile strength of from 0.1 to 50 kg/sq.cm. and a percentage elongation of from 5 to 500%.

The invention will be further understood from the following exemplary embodiments thereof illustrating various possible compositions of the proposed adhesive.

EXAMPLE 1

In this example, the adhesive for gluing together soft body tissues has the following composition, wt.%:

toluylenediisocyanate, 1
macrodiisocyanate comprising toluylenediisocyanate and polyhydroxypropyleneglycol radicals, 98.9
2,4,6-tris(dimethylaminomethyl)phenol, 0.1.

The adhesive was employed for repairing linear incisions of the skeletal muscles in rabbits and albino rats. After adhesive had been introduced into the wound, the wound edges were approximated with forceps. 3 to 5 minutes later the adhesive suture was found to be sufficiently strong.

EXAMPLE 2

In this example, the adhesive had the following composition, wt.%:

toluylenediisocyanate, 10
macrodiisocyanate comprising toluylenediisocyanate and polyhydroxyethyleneglycol radicals, 70
2,4,6-trist(dimethylaminomethyl)phenol, 20.

The adhesive was employed for plastic repair of aponeurosis of the anterior abdominal wall. The sheaths of the anterior abdominal wall dissected as far as the peritoneum were smeared with the adhesive and lap-joined. Tested for shear strength, the adhesive suture was found to be 800 to 1,200 g/sq.cm.strong for 1 to 7 days.

EXAMPLE 3

In this example, the adhesive had the following composition, wt.%:

4,4'-diphenylmethanediisocyanate, 5
macrodiisocyanate comprising radicals of toluylenediisocyanate and of the copolymer of propyleneglycol with ethyleneglycol, 85
2,4,6-tris(dimethylaminomethyl)phenol, 10.

The adhesive was employed for repairing linear incisions of the skeletal muscles and kidneys (dissected as far as the renal pelvis). The renal artery was clamped for 2 to 3 minutes. The adhesive provided for a secure joint, caused a moderate inflammatory reaction, and was eliminated within 6 to 8 months.

EXAMPLE 4

In this example, the adhesive had the following composition, wt.%:

naphthylenediisocyanate, 1
macrodiisocyanate comprising radicals of 4,4'-diphenylmethanediisocyanate and of the copolymer of tetramethyleneglycol with propyleneglycol, 98
2,4,6-tris(dimethylaminomethyl)phenol, 1.

The adhesive was employed for closing experimental colonic fistulas by being introduced into the fistular channel via a probe.

Strength testing by the pneumopressure technique indicated that 10 to 12 days postoperatively the suture proved stronger than the normal sections of the colon.

EXAMPLE 5

In this example, the adhesive had the following composition, wt.%:

toluylenediisocyanate, 1
macrodiisocyanate comprising toluylenediisocyanate and polydiethyleneglycolsebacate radicals, 98.9
2,4,6-tris(dimethylaminomethyl)phenol, 0.1.

The adhesive was employed to provide a protective coating on incised skin-muscle wounds, securing the latter from infection and thereby providing for the healing thereof.

EXAMPLE 6

In this example, the adhesive has the following composition, wt.%:

toluylenediisocyanate, 30
macrodiisocyanate comprising toluylenediisocyanate and polydiethyleneglycoladipinate radicals, 60
2,4,6-tris(dimethylaminomethyl)phenol, 10.

The adhesive was employed as a haemostatic means while resecting a section of the liver and the renal pole of rabbits. The adhesive formed on the wound surface a porous polymeric film which was subsequently intergrown with connective tissue elements. The function of the kidneys was back to normal within 3 to 4 weeks.

EXAMPLE 7

In this example, the adhesive had the following composition, wt.%:

4,4'-diphenylmethanediisocyanate, 20
macrodiisocyanate comprising naphthylenediisocyanate and polyhydroxypropyleneglycol radicals, 65
2,4,6-tris(dimethylaminomethyl)phenol, 15.

The adhesive was employed to provide a polymeric coating around the jugular veins of the experimental animals, simulating aneurysm therapy. The adhesive caused a moderate inflammatory reaction of the vessel and, with time, was largely replaced by a connective-tissue framework.

EXAMPLE 8

In this example, the adhesive had the following composition, wt.%:

4,4'-diphenylmethanediisocyanate, 50
macrodiisocyanate comprising toluylenediisocyanate and polyethyleneglycoladipinate radicals, 48
2,4,6-tris(dimethylaminomethyl)phenol, 2.

The adhesive was employed for closing bronchial fistulas following lung resection in dogs by introducing adhesive into the bronchus via a bronchoscope, the "adhesive plug" being formed securely closing the bronchial fistula.

EXAMPLE 9

In this example, the adhesive had the following composition, wt.%:

4,4'-diphenylmethanediisocyanate, 10
macrodiisocyanate comprising 4,4'-diphenylmethanediisocyanate and polytetramethyleneglycol radicals, 89.5
2,4,6-tris(dimethylaminomethyl)phenol, 0.5.

The adhesive was employed for reinforcing the sutures and sealing the gastroenteroanastomosis in dogs. The adhesive was securely affixed to the tissues, providing for a reliable sealing. The inflammatory reaction of the tissues was moderate.

EXAMPLE 10

In this example, the adhesive had the following composition, wt.%:

phenyldiisocyanate, 5
macrodiisocyanate comprising radicals of 4,4'-diphenylmethanediisocyanate and the copolymer of tetramethyleneglycol with ethyleneglycol, 80
2,4,6-tris(dimethylaminomethyl)phenol, 15.

The adhesive was employed for closing incised wound of the liver. The setting time was 5 minutes. The wound edges were approximated with the aid of a single silk ligature. The adhesive was eliminated from the body within 12 months.

EXAMPLE 11

In this example, the adhesive had the following composition, wt.%:

4,4'-diphenylmethanediisocyanate, 50
macrodiisocyanate comprising toluylenediisocyanate and polypropyleneglycoladipinate radicals, 30
2,4,6-tris(dimethylaminomethyl)phenol, 20.

The adhesive was employed as a protective dressing for wound and burn surfaces, providing favourable conditions for reparative-regenerative processes.

What is claimed is:

1. An adhesive for gluing together soft body tissues, which has the following composition, wt.%:
aromatic diisocyanate, from 1 to 50
macrodiisocyanate of the general formula $$NCO-R-NHCO-R'-NHCO-R-NCO,$$
$$\phantom{NCO-R-N}\underset{O}{\|}\phantom{R'-N}\underset{O}{\|}$$

where
R is an aromatic diisocyanate radical
R' is a polyether or polyester radical, from 98.9 to 30
2,4,6-tris(dimethylaminomethyl)phenol, from 0.1 to 20.

2. An adhesive as set forth in claim 1, wherein the aromatic diisocyanate is selected from the group consisting of toluylenediisocyanate, 4,4'-diphenylmethanediisocyanate and naphthylenediisocyanate.

3. An adhesive as set forth in claim 1, wherein the macrodiisocyanate has the formula

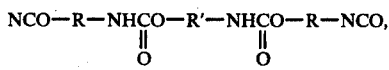

where
R is a radical of an aromatic diisocyanate selected from the group consisting of toluylenediisocyanate, 4,4'-diphenylmethanediisocyanate and naphthylenediisocyanate;
R' is a radical of a polyester selected from the group consisting of polydiethyleneglycoladipate, polyethyleneglycoladipate and polydiethyleneglycolsebacate.

4. An adhesive as set forth in claim 1, wherein the macrodiisocyanate has the formula

NCO—R—NHCO—R'—NHCO—R—NCO,
         ‖              ‖
         O              O where
R is a radical or an aromatic diisocyanate selected from the group consisting of toluylenediisocyanate, 4,4'-diphenylmethanediisocyanate and naphthylenediisocyanate;
R' is a radical of a polyether selected from the group consisting of polyhydroxypropyleneglycol, polyhydroxyethyleneglycol, polytetramethyleneglycol, the copolymer of propyleneglycol with ethyleneglycol, and the copolymer of propyleneglycol with tetramethyleneglycol.

5. An adhesive for gluing together soft body tissues, which has the following composition, wt.%:
toluylenediisocyanate, 10
macrodiisocyanate of the formula

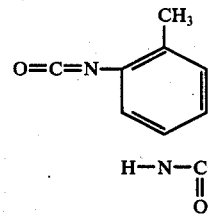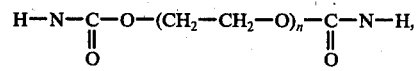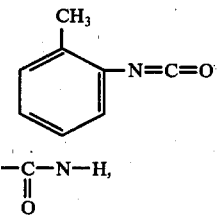

2,4,6-tris(dimethylaminomethyl)phenol, 20.

6. An adhesive for gluing together soft body tissues, which has the following composition, wt.%:
toluylenediisocyanate, 10
macrodiisocyanate of the formula

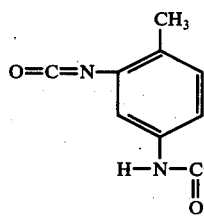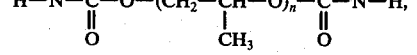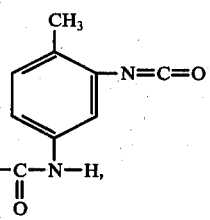

2,4,6-tris(dimethylaminomethyl)phenol, 10.

* * * * *